May 17, 1960 F. MEILLAND Plant Pat. 1,944
ROSE PLANT
Filed Feb. 16, 1959
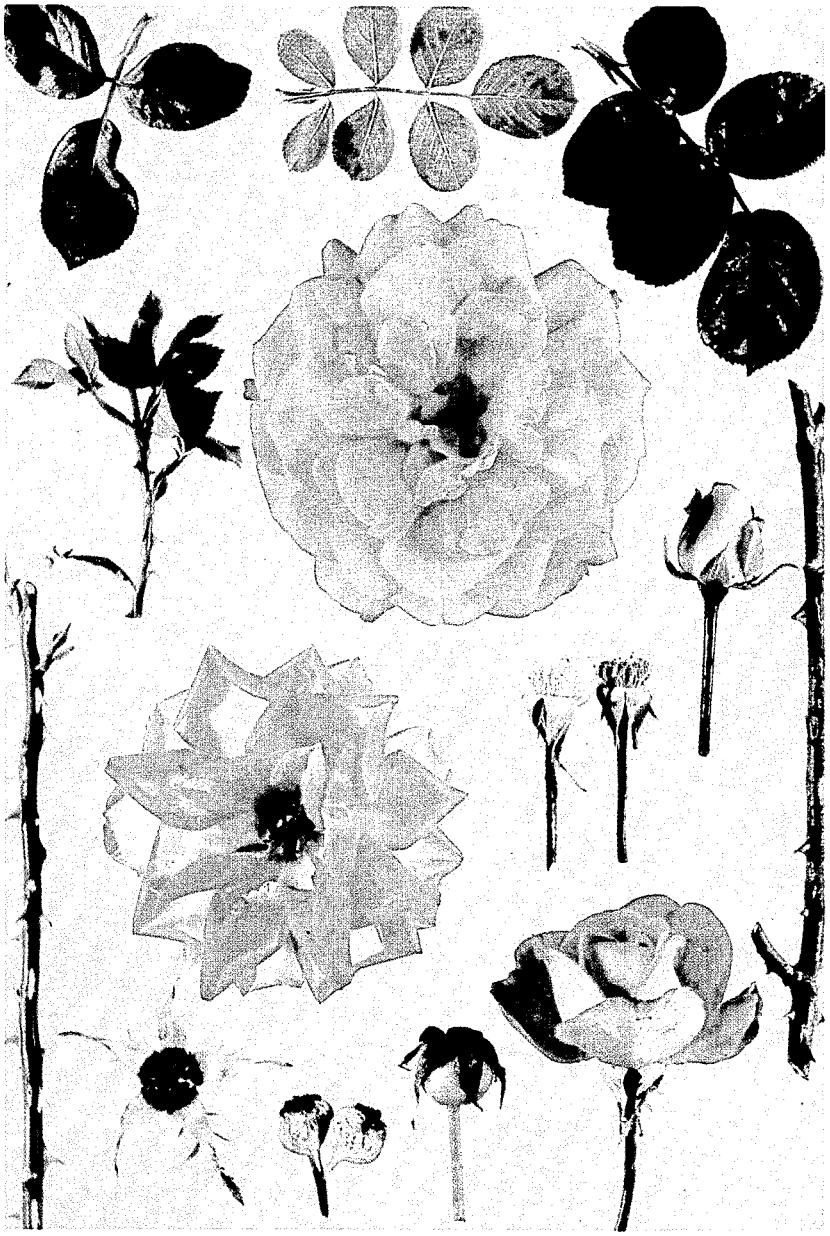
INVENTOR
Francis Meilland, Deceased
By: Marie Louise Meilland, née Paolino
Legal Representative
BY Robb & Robb
ATTORNEYS United States Patent Office Plant Pat. 1,944
Patented May 17, 1960

1,944

ROSE PLANT

Francis Meilland, deceased, late of Cap d'Antibes, Alpes Maritimes, France, by Marie Louise Meilland, née Paolino, legal representative, Cap d'Antibes, France, assignor to The Conard-Pyle Company, West Grove, Pa., a corporation of Pennsylvania Application February 16, 1959, Serial No. 793,655

Claims priority, application France June 16, 1958

1 Claim. (Cl. 47—61)

The present invention relates to a new and distinct variety of rose plant of the hybrid tea class, which was originated by the applicant by crossing the variety "Henri Mallerin" (U.S. Plant Patent No. 1,349) with an unnamed and unpatented seedling of "Happiness"—known in France as "Rouge Meilland" (U.S. Plant Patent No. 911) × "Floradora" (unpatented).

The primary objective of this breeding was to produce a new rose variety which would retain the brilliant coloring of the unnamed seedling parent while eliminating its tendency to acquire magenta color tones in the later stages of bloom life. This objective was fully achieved, along with other desirable features which, in combination, are outstanding in the new variety and distinguish it from its parents as well as from all other varieties of which the applicant was aware:

(1) A vigorous, upright habit of growth;

(2) Large, well-formed and long-lasting blooms borne on stems long enough for cutting;

(3) A color intensity which is retained to maturity with little tendency to the formation of undesirable magenta color tones; and (4) A distinctive and unique glowing Turkey Red general color tonality of the blooms, with the reverse of the petals Yellow Ochre lightly overcast with Jasper Red.

Asexual reproduction of the new variety by budding, as performed in France and at West Grove, Pennsylvania, U.S.A., shows that the foregoing characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with the Horticultural Color Chart of the Royal Horticultural Society, except where general color terms of ordinary dictionary significance are obvious:

Type: Hardy; bush; outdoor; seedling; for cut flowers and for garden decoration.

Class: Hybrid tea.

Breeding: Seedling.

*Seed parent.*—"Henri Mallerin."

*Pollen parent.*—An unnamed seedling of "Happiness" × "Floradora."

Propagation: Holds its distinguishing characteristics through succeeding propagations by budding.

*Flower*

Locality where grown and observed: West Grove, Pennsylvania, U.S.A.

Flowers borne: Singly to stem; on stems of normal strength and from medium length to long.

Quantity of bloom: Free, outdoors.

Continuity: Continuous.

Fragrance: Slight. Nature—tea.

Bud:

*Peduncle.*—Medium length; medium caliper; erect; stiff; rough; with medium number of prickles. Color—Garnet Brown, Plate 00918/3 overlaying Lettuce Green, Plate 861/1.

*Before calyx breaks.*—Size—medium. Form—medium length; ovoid; with a conspicuous neck; with foliaceous appendages on the surface of the bud; with medium stout, bristle-like foliaceous parts extending beyond the tip of the bud equal to ¼ or more of its length.

*As calyx breaks.*—Color—Oxblood Red, Plate 00823.

*As first petal opens.*—Size—large. Form—medium length; pointed-ovoid. Color: outside—Indian Lake, Plate 826 where first exposed to the light, irregularly underlaid with Blood Red, Plate 820; petal area not exposed to light Scarlet, Plate 19; inside—Chrysanthemum Crimson, Plate 824 on side margin of petal, grading to Cardinal Red, Plate 822 over the central area from the apex toward the base where it grades into Lemon Yellow, Plate 4 at point of attachment.

*Opening.*—Opens up well.

Bloom:

*Size (when fully open).*—Large; from 4¾ inches to 5¼ inches.

*Petalage.*—Very double; from 55 to 60 petals; arranged regularly.

*Form.*—Full and high-centered at first and remaining full; petals being at first loosely rolled outward and remaining loosely rolled outward at maturity.

Petals: Leathery; with inside satiny and outside shiny.

*Shape.*—Outer — obovate. Intermediate — obovate. Inner—undulate; irregular.

This description of a newly opened flower was made from a rose grown outdoors in the month of September at West Grove, Pennsylvania, U.S.A.:

*Color.*—Outer petal: outside surface—variable from Rose Bengal, Plate 25/2 to Erythrite Red, Plate 0027, irregularly streaked or washed with Phlox Pink, Plate 625/3, with point of attachment Sulphur Yellow, Plate 1; inside surface—Cardinal Red, Plate 822 over main portion of petal, becoming Spinel Pink, Plate 0625; basal area Aureolin, Plate 3. Intermediate petal: outside surface—Yellow Ochre, Plate 07/2, lightly overcast with Jasper Red, Plate 018/1 over the margin of petal and sometimes shading to Claret Rose, Plate 021/1, with veining Jasper Red, Plate 018/1; base of petal Straw Yellow, Plate 604; inside surface—Turkey Red, Plate 721, grading to Scarlet, Plate 19 over basal quarter of petal; base of petal Aureolin, Plate 3. Inner petal: outside surface—Yellow Ochre, Plate 07/2, very lightly overcast with Jasper Red, Plate 018/2 at margin of petal and veined with Jasper Red, Plate 018/2; basal quarter of petal Straw Yellow, Plate 604; inside surface—Turkey Red, Plate 721, grading to Mandarin Red, Plate 17/1; base of petal Aureolin, Plate 3.

This description was made from a rose that was open for 3 days outdoors in the month of September at West Grove, Pennsylvania, U.S.A.:

*Color.*—Outer petal: outside surface—Rose Bengal, Plate 25/2 covering upper half of petal, with lower half of petal Naples Yellow, Plate 403/2; base of petal Mimosa Yellow, Plate 602/1; inside surface—Rose Red, Plate 724 at margin, overlaying Spirea Red, Plate 025, with basal half of petal Crimson, Plate 22/1; base of petal Aureolin, Plate 3. Inner petal: outside surface—Solferino Purple, Plate 26 extending as a thin margin around the petal, grading to Rose Bengal, Plate 25/2 over upper half of petal, with basal half of petal Naples Yellow, Plate 403/2; base of petal Mimosa Yellow, Plate 602; inside surface—Rose Red, Plate 724, grading to Spirea Red, Plate 025 and to Spirea Red, Plate 025/2 over basal area; base of petal Aureolin, Plate 3.

*General color effect.*—Newly opened flower—a velvety Turkey Red, Plate 721, with reverse of petals Yellow Ochre, Plate 07/2. 3-days open—Rose Red, Plate 724, tinted with Spirea Red, Plate 025.

*Behavior.*—Drop off cleanly.

*Flower longevity.*—On bush in garden—4 days in August. Cut roses grown outdoors and kept at living room temperatures—5 days in August.

*Reproductive organs*

Stamens: Medium number; arranged regularly about pistils.

Filaments: Many—most with anthers; medium length. Color—Lemon Yellow, Plate 4.

Anthers: All open at once; medium size; occasionally an anther fused with a petaloid. Color—Lemon Yellow, Plate 4.

Pollen: Moderate abundance. Color—gold.

Pistils: Medium number.

Styles: Uneven; medium length; medium caliper; bunched.

Stigma: Color—whitish yellow.

Ovaries: All enclosed in receptacle.

Hips: None observed.

Sepals: Permanent; moderately long; spear-shaped.

Seeds: None observed.

*Plant*

Foliage:

*Leaves.*—Compound of 3, 5 and 7 leaflets; abundant; medium size; leathery; glossy.

*Leaflets.* — Shape — oval, with apex acuminate. Base—obtuse. Margin—simply serrate.

*Color.*—Mature: upper surface—Spinach Green, Plate 0960/1; under surface—Willow Green, Plate 000862/1. Young: upper surface—Fern Green, Plate 0862, overlaid with Garnet Brown, Plate 00918; under surface—Spinach Green, Plate 0960/3, overlaid with Oxblood Red, Plate 00823/3.

*Rachis (the supporting stem of the compound leaf).*—Medium caliper. Upper side—grooved; hairy. Under side—sparsely prickly.

*Stipules.*—Moderately long; narrow; with moderately short points turning out at an angle of more than 45°.

*Disease resistance.*—Comparable to that of the average variety grown under the same cultural conditions at West Grove, Pennsylvania, U.S.A.

Growth:

*Habit.*—Upright; much-branched.

*Growth.*—Vigorous.

*Canes.*—Moderately heavy.

*Main stems.*—Dull. Color—Spinach Green, Plate 0960/1. Prickles—several; color—Fern Green, Plate 0862, flushed with Rhodonite Red, Plate 0022. Hairs—none.

*Branches.*—Dull. Color — Spinach Green, Plate 0960/1. Prickles—several; color—Fern Green, Plate 0862, flushed with Rhodonite Red, Plate 0022. Hairs—none.

*New shoots.*—Dull. Color—Lettuce Green, Plate 861/1, overlaid with Erythrite Red, Plate 0027. Prickles—several; color—Erythrite Red, Plate 0027. Hairs—none.

What is claimed is:

A new and distinct variety of rose plant of the hybrid tea class, substantially as herein shown and described, characterized particularly as to novelty by the unique combination of a vigorous, upright habit of growth, large, well-formed and a long-lasting blooms borne on stems long enough for cutting, a color intensity which is retained to maturity with little tendency to the formation of undesirable magenta color tones, and a distinctive glowing Turkey Red general color tonality of the blooms, with the reverse of the petals Yellow Ochre, lightly overcast with Jasper Red.

No references cited.